United States Patent [19]

Huber, Jr.

[11] 4,264,525

[45] Apr. 28, 1981

[54] STEPWISE REDUCTION OF P-NITROPHENOL

[75] Inventor: John Huber, Jr., Mahwah, N.J.

[73] Assignee: Penick Corporation, Lynhurst, N.J.

[21] Appl. No.: 53,888

[22] Filed: Jul. 2, 1979

[51] Int. Cl.³ .................... C07C 103/32; C07C 89/00; C07C 85/11
[52] U.S. Cl. ..................................... 564/223; 564/418
[58] Field of Search ........................... 260/562 A, 575

[56] References Cited

U.S. PATENT DOCUMENTS

| | | | |
|---|---|---|---|
| 2,799,692 | 7/1957 | Croxall et al. | 260/562 A X |
| 2,945,870 | 7/1960 | Young | 260/562 A X |
| 3,042,719 | 7/1962 | Hahn et al. | 260/562 A |
| 3,076,030 | 1/1963 | Freifelder | 260/562 A |
| 3,177,256 | 4/1965 | Holtzclaw et al. | 260/575 |
| 3,341,587 | 9/1967 | Duesel et al. | 260/562 A |

*Primary Examiner*—John Doll
*Attorney, Agent, or Firm*—David H. LeRoy

[57] ABSTRACT

A stepwise reduction and acetylation process for the production of pure N-acetyl-p-aminophenol (APAP) from p-nitrophenol in an aqueous system that avoids the need for strong acids or excess acetic anhydride.

22 Claims, No Drawings

STEPWISE REDUCTION OF P-NITROPHENOL

FIELD OF INVENTION

This invention relates to the production of p-aminophenol and N-acetyl-p-aminophenol.

BACKGROUND OF INVENTION

N-acetyl-p-aminophenol (APAP) is a known compound widely used as an analgesic and anti-pyretic agent in various therapeutic preparations. A commercial method for preparing N-acetyl-p-aminophenol involves reduction of p-nitrophenol to p-aminophenol and then acetylation wherein the p-aminophenol is dispersed in a non-aqueous solvent and/or excess acetic anhydride.

The conventional process for the reduction of p-nitrophenol to produce p-aminophenol involves catalytically hydrogenating the p-nitrophenol in the presence of strong acids such as sulfuric, hydrochloric and phosphoric acids as shown in U.S. Pat. No. 2,198,249. Other acids such as oxalic or sulfonic acids as disclosed in U.S. Pat. No. 2,525,515 have been used. Metal catalysts used for reduction include aluminum as in U.S. Pat. No. 2,525,515; platinum, palladium or noble metal catalysts and their oxides as described in U.S. Pat. Nos. 2,947,781; 3,076,030; 3,079,435; 3,328,465; 3,383,416; 3,654,365 and 3,383,416; and molybdenum sulfide or platinum sulfide-on-carbon as in U.S. Pat. No. 3,953,309.

In all of these methods, the p-aminophenol which is obtained is relatively impure and requires substantial purification before it can be further used in the production of APAP. Unfortunately, by-products are formed in the reduction of the p-nitrophenol and in the acetylation which lead to off-color and impure APAP thus requiring further purification and crystallization steps to produce an acceptable product as described in U.S. Pat. Nos. 3,658,905; 3,694,508; 3,703,598; 3,717,680; 3,845,129; 3,876,703; and 3,953,283.

Attempts to overcome the discoloration and by-product formation by various techniques have not been entirely successful or economical. The use of a reducing atmosphere and non-oxidizing acids is described in U.S. Pat. Nos. 3,177,250; 3,042,719 and 3,223,727. More recently simultaneous reduction of p-nitrophenol and acetylation of the p-aminophenol product while using an acetic acid solvent or acetic anhydride solvent system without prior isolation of the p-aminophenol has been reported as in U.S. Pat. Nos. 3,076,030 and 3,341,587.

The principle method for the preparation of p-nitrophenol may begin with nitration and chlorination of benzene to produce p-chloronitrobenzene. The p-chloronitrobenzene then is subjected to alkaline hydrolysis to produce the p-nitrophenol. The p-nitrophenol must be purified and separated from the hydrolysate before it can be used to prepare acceptable APAP according to the conventional processes.

Heretofore in the preparation of N-acetyl-p-aminophenol (APAP) it has been necessary to use corrosive strong acids, such as sulfuric, requiring costly neutralization steps producing salts to be removed in purification and possible problems with salt disposal or the use of expensive non-aqueous salt systems. Moreover, expensive and laborious purification procedures were required for p-nitrophenol, p-aminophenol and the APAP to insure an acceptably pure APAP product for therapeutic preparations.

SUMMARY OF THE INVENTION

In accordance with this invention, a stepwise process is provided for the production of N-acetyl-p-aminophenol from p-nitrophenol which comprises the steps of:

(a) hydrogenating p-nitrophenol in an aqueous solvent system in the absence of acetic anhydride to convert a portion of said p-nitrophenol to p-aminophenol while maintaining the reaction pH below about 7.0;

(b) treating the reaction mixture of step (a) with acetic anhydride to affect acetylation of the p-aminophenol without isolation of said p-aminophenol wherein acetic acid produced during acetylation is sufficient to maintain said pH; and (c) recovering the N-acetyl-p-aminophenol from the reaction product of step (b).

In another embodiment, the present invention is also directed to an improved process for the production of N-acetyl-p-aminophenol which comprises subjecting p-chloronitrophenol to alkaline hydrolysis to produce p-nitrophenol, adding a sufficient amount of borate ion to interact with undesirable by-products of said alkaline hydrolysis, reducing the borate ion containing p-nitrophenol hydrolysis product in the presence of a palladium catalyst to partially convert a portion of said p-nitrophenol to p-aminophenol, acetylating the p-aminophenol to N-acetyl-p-aminophenol, and recovering N-acetyl-p-aminophenol, characterized in that said reducing and acetylating proceeds in a stepwise manner at a pH below about 7.0 and a temperature from about 65° C. to about 75° C. until the conversion of available p-nitrophenol to N-acetyl-p-aminophenol is completed.

It has unexpectedly been discovered that through the practice of this invention, high purity N-acetyl-p-aminophenol of acceptable quality and without discoloration can be produced using a stepwise hydrogenation of p-nitrophenol and acetylation of p-aminophenol procedure without the need for a non-aqueous solvent or isolation of p-nitrophenol or p-aminophenol intermediates. This stepwise procedure depends upon maintaining the pH of the aqueous medium below about 7.0 during the entire hydrogenation and acetylation. A borate ion additive present during the hydrogenation and acetylation assists in buffering the aqueous solution and provides an unexpected control over side reactions or by-products.

Moreover, it has also unexpectedly been found that impure p-nitrophenol hydrolysate can be directly hydrogenated and acetylated in a stepwise manner if borate ion is present without the formation of undesirable by-products or color formation and that a highly purified N-acetyl-p-aminophenol (APAP) may be thereby obtained. The elimination of the conventional purification step for the p-nitrophenol containing hydrolysate (i.e. from the hydrolysis of p-chlorobenzene) and the elimination of excess acetic anhydride and strong acids is a commercially significant development in the production of high purity N-acetyl-p-aminophenol.

DESCRIPTION OF PREFERRED EMBODIMENTS

The present invention enables the use of an aqueous system and a mild acid for the production of N-acetyl-p-aminophenol (APAP) from p-nitrophenol. According to this invention a portion of the total p-nitrophenol is reduced to p-aminophenol in an aqueous system, the reduction then interrupted for acetylation of the p-aminophenol and the reduction resumed or completed. Finally, all the p-aminophenol produced is acetylated to produce APAP of excellent purity in high yields of at least about 80%.

In conventional processes for the production of N-acetyl-p-aminophenol strong or expensive acids are added to p-nitrophenol to control the reduction. Unfortunately costly neutralization and salt removal steps are then involved in purification of the N-acetyl-p-aminophenol. It would be desirable if the use of such acids could be avoided. Nevertheless, it has been found that reduction of p-nitrophenol in water in the absence of added acids and acetylation of the p-aminophenol product results in the production of off-color and impure N-acetyl-p-aminophenol.

It has now unexpectedly been found that, if reduction of p-nitrophenol in an aqueous system is interrupted, so that pH never rises above about 7, by direct acetylation of the reaction mixture with acetic anhydride, N-acetyl-p-aminophenol of acceptable purity and color may be produced without the need for additional acids. Since the mechanisms involved in production of high purity N-acetyl-p-aminophenol are complicated, applicant does not wish to be bound by any theory. In the reaction of acetic anhydride with p-aminophenol, one mole of acetic acid per mole of N-acetyl-p-aminophenol is produced. The presence of the acetic acid produced from the acetic anhydride reaction is sufficient to maintain the pH below about 7.0. Thus, by the stepwise reduction and acetylation of the instant invention, no additional or expensive acids are required beyond that generated from the acetylation and high quality N-acetyl-p-aminophenol is produced in an aqueous system.

Direct acetylation of the reduction product and minimization of undesirable side effects is possible operating at below about 110° C. and below about pH 7.0 in the stepwise manner of this invention. Moreover, if the temperature is preferably held to a temperature of from about 65° to about 75° C. during stepwise hydrogenation and stepwise acetylation, a high purity acceptable APAP can be obtained using an aqueous solvent system. The process may be carried out at a hydrogen pressure from slightly above atmospheric pressure to several hundred atmospheres. Preferably a hydrogen pressure of from about 60 to about 80 psi is used. The pH during the stepwise hydrogenation/acetylation is preferably maintained near the solution pH for p-nitrophenol or from about 2.5 to about 7.0. If the pH goes above about 7.0, the final APAP product contains undesirable by-products and color bodies and requires further purification.

It is preferred to interrupt reduction of the p-nitrophenol at least at about 20%, and most preferably at about 50 to about 60% conversion to p-aminophenol. Acetylation of the p-aminophenol is then brought about by direct addition of acetic anhydride to the reaction mixture. Then, reduction is continued, followed by acetylation, proceeding stepwise until hydrogenation and acetylation is completed. Preferably this can be accomplished in two steps or more if desired, as long as the pH is maintained below about 7.0 by the reaction of the acetic anhydride. Moreover, other acids may be present during reduction and acetylation, but large quantities of other acids are not desirable from an economic point of view as previously discussed.

Another embodiment of the present invention relates to the presence of borate ion during the stepwise reduction of the p-nitrophenol and acetylation of the p-acetaminophenol. As previously discussed, it has been found that if purified p-nitrophenol is the starting material for the stepwise process of this invention, then a highly pure N-acetyl-p-aminophenol can be produced. Nevertheless, it would be desirable if one could proceed directly from p-chloronitrobenzene without separation and purification of the p-nitrophenol.

It has now been found that the presence of borate ion during stepwise reduction of p-nitrophenol and acetylation of p-aminophenol permits the production of highly pure N-acetyl-p-aminophenol in an aqueous system without laborious purification steps for the p-nitrophenol or the p-aminophenol.

One commercial route to the production of N-acetyl-p-aminophenol involves the following steps:

(1) Hydrolysis of p-chloronitrobenzene to produce p-nitrophenol,
(2) Separation and purification of p-nitrophenol,
(3) Reduction of the p-nitrophenol to p-aminophenol,
(4) Separation and purification of the p-aminophenol,
(5) Acetylation of the p-aminophenol to produce N-acetyl-p-aminophenol,
(6) Separation and purification of p-acetaminophenol.

Therefore, according to the process of the instant invention, a source of borate ion, such as boric acid or boric acid salts is added to the hydrolysate product containing the nitrophenol before the stepwise hydrogenation and acetylation procedure for production of N-acetyl-p-aminophenol. The presence of the boric acid may also assist to a small extent in a buffering type action to maintain the desirable pH during the stepwise hydrogenation and acetylation. Preferably, the boric acid is added to the p-chloronitrobenzene before or during the subsequent hydrolysis and the p-nitrophenol containing hydrolysate used directly for the stepwise hydrogenation and acetylation process for production of highly purified APAP.

Here again, applicants do not wish to be bound by any theory. Nevertheless, it appears the borate ion forms some complex with by-products produced in the hydrolysis of p-chloronitrobenzene and that the borate complex avoids undesirable side effects and discolorations that normally occur and in the subsequent stepwise hydrogenation and acetylation process of this invention. It is, therefore, further believed that there are at least two sources for impurities and discoloration during the production of N-acetyl-p-aminophenol, i.e. one source arising during hydrolysis of the p-chloronitrobenzene and the other originating during hydrogenation of the p-nitrophenol at basic pH.

The alkaline hydrolysis of p-chloronitrobenzene produces a suspension of sodium p-nitrophenol in a sodium chloride solution. To insure uniformity in the composition prior to reduction, the sodium-para-chloronitrobenzene preferably may be centrifuged and reconstituted for reduction. Nitrites produced in the hydrolysis are preferably destroyed by addition of sulfamic acid and the neutralization of the sodium form, which occurs at about pH 2.5, accomplished by addition of sulfuric acid. Similarly the p-nitrophenol may be treated with charcoal before hydrogenation. In conventional processes, soluble by-products remain with the p-nitrophenol solution and normally result in formation of undesirable reactants and color bodies if the p-nitrophenol is not further purified as by distillation before the stepwise hydrogenation and acetylation. Moreover, the use of various acids during reduction, such as sulfuric, hydrochloric, phosphoric, or milder organic acids such as oxalic or acetic do not overcome the deleterious effect of direct stepwise hydrogenation of the p-nitrophenol produced as thus described. Unexpectedly, it has been found that addition of borate ion or boric acid to the thus produced non-purified p-nitrophenol followed by the stepwise reduction and acetylation overcomes the undesirable side reactions and permits production of an acceptable highly pure N-acetyl-p-aminophenol product.

The amount of boric acid used must be sufficient to complex by-products that lead to undesirable side reactions and color formation. Thus, from about 0.5 to about 20 mole percent based on p-nitrophenol may be used. Preferably, from about 10 to about 15 mole percent based on p-nitrophenol is used for proceeding from the p-chloronitrobenzene hydrolysate. The borate ion may be introduced at different points in the APAP synthesis. For example, it may be added before, during or after the hydrolysis of the p-chloronitrobenzene. For elimination of undesirable reactions and color formation, borate ion must be present during the hydrogenation stage of the stepwise hydrogenation and acetylation process of this invention, if proceeding from a non-purified p-nitrophenol and to provide maximum benefit of the complexing activity.

The hydrogenation catalyst preferred for the reduction of the p-nitrophenol to p-aminophenol is palladium-on-carbon. Other hydrogenation catalysts may be used without affecting the overall process of this invention. For example, nickel, platinum, palladium or noble metal catalysts and their oxides may be used.

In determining purity of the N-acetyl-p-aminophenol, the caustic test and granulation test were employed. In the caustic test 100 mg. of N-acetyl-p-aminophenol is placed in a 5.0 ml. volumetric flask and diluted to volume with a 10% sodium hydroxide solution. A completely colorless solution upon the dissolution of the N-acetyl-p-aminophenol indicates acceptable pharmaceutical quality.

In the granulation test 10.0 gm. of N-acetyl-p-aminophenol (ground to 100 mesh) is placed in a 50 ml. beaker and 10.0 ml. of water is added to make a level paste. The paste is heated for 2½ hours at 50°–55° C. and then cooled to room temperature. No discoloration of the hardened mass indicates acceptable pharmaceutical purity. Any pink, yellow or gray discoloration indicates impure N-acetyl-p-aminophenol.

Thus as previously described, if the N-acetyl-p-aminophenol product is discolored, it is impure. A white product or colorless product solution would indicate purity, but not necessarily an acceptable purity for a pharmaceutical grade material. For a pharmaceutical grade purity, the N-acetyl-p-aminophenol product should be white and also pass the caustic test and the granulation test as set forth in the above description.

The invention is illustrated by the following examples which, however, are not to be taken as limiting in any respect.

EXAMPLE I

Stepwise Reduction at 95°–98° C.

In the calculation of the crude yield the actual weight in grams of the recovered APAP is divided by the theoretical yield of APAP in grams. The theoretical yield is calculated by multiplying the weight in grams of the starting material (p-nitrophenol) by the ratio of the molecular weight of APAP to the molecular weight of p-nitrophenol. Similarly the weight in grams of the APAP recovered from recrystalization divided by the theoretical yield provides the recrystalized yield.

This example shows the stepwise reduction of p-nitrophenol and acetylation of p-aminophenol to produce the N-acetyl-p-aminophenol according to this invention: 90 grams of p-nitrophenol was added to 243 ml of water containing 1.25 grams charcoal and 0.31 grams catalyst (50% catalyst 50% water) of 5% palladium-on-charcoal. The system was heated to 95°–98° C. and hydrogen pressure of 70 psig. After 1 hour hydrogenation, the batch was cooled to 48° C. (pH 5.8) and 35 grams acetic anhydride was added. The reduction was continued at 95°–98° C. and 70 psig until hydrogen uptake ceased. The batch was cooled to 40° C. (pH 5.0) and 35 grams of acetic anhydride was added with heating to 95° C. The batch was filtered to recover catalyst. The N-acetyl-p-aminophenol was crystallized to yield a white crystalline product. Quality of the APAP was good giving only a slight pink caustic test and the product yield was 81.2%.

EXAMPLE II

Stepwise Reduction at 65°–70° C.

This example illustrates the production of a high quality APAP product according to this invention: 90 grams of p-nitrophenol was added to 243 ml of water containing 1.25 grams charcoal and 0.31 grams wet 5% palladium-on-charcoal catalyst (50% catalyst;50% water). The system was heated to 65°–70° C. and hydrogen pressure of 70 psig. After 1 hour hydrogenation, the batch was cooled to 48° C. (pH 5.8) and 35 grams acetic anhydride was added. The reduction was continued at 65°–70° C. and 70 psig until hydrogen uptake ceased. The batch was cooled to 40° C. (pH 5.0) and 35 grams of acetic anhydride was added with heating to 95° C. The batch was filtered to recover catalyst. The N-acetyl-p-aminophenol was crystallized to give a 69.7% yield and was of excellent quality and passed the granulation and caustic tests.

EXAMPLE III

Non-Acid Aqueous Reduction

The following comparative examples illustrates that reduction of p-nitrophenol in an aqueous system results in a basic pH and that acetylation of the p-aminophenol produced impure, discolored, and non-acceptable N-acetyl-p-aminophenol: Sodium p-nitrophenol in water at 60°–65° C. was reduced with hydrogen at 30–35 psi to p-aminophenol using a 5% palladium-on-carbon catalyst. Alkalinity after reduction was pH 12.5. Sulfuric acid was added to adjust to acidic condition for acetylation and the product filtered to recover the catalyst. Acetic anhydride was added to produce the N-acetyl-p-aminophenol. Ammonia was added to neutralize the acid and the N-acetyl-p-aminophenol crystallized. The color of the crystals of APAP was off-white and the caustic test deep purple. Product yield was 62.8%.

The procedure was repeated three additional times and the p-aminophenol formed was washed with toluol and/or aniline. In each case the quality of the APAP was unacceptable.

These examples demonstrate the problems and undesirable effects caused by reduction of p-nitrophenol in an aqueous solvent without the presence of acids or the stepwise process set forth in this invention for the production of high purity acetyl-N-aminophenol.

EXAMPLE IV

Large Scale Production of APAP by Stepwise Reduction Using the Borate Ion

This example illustrates the large scale production of APAP according to the process of this invention: *p-Nitrophenol Supply*—3800 lbs. of p-nitrophenol from the alkaline hydrolysis of p-chloronitrobenzene was dispersed in 450 gal. of water and heated to 50° C. and diluted with 200 gal. of water prior to hydrogenation; *Boric Acid/Charcoal Supply*—170 lbs. of boric acid and 50 lbs. of carbon were dispersed in 450 gal. of water and diluted with 200 gal. of water before hydrogenation.

Hydrogenator

The p-nitrophenol supply and the boric acid/charcoal supply were added to the hydrogenator with 4–6 kilograms of 5% palladium-on-charcoal. The hydrogenator was charged with 3500 ft.$^3$ of hydrogen at 70 psig cooling to 60° C. and held until about 60% completion of the hydrogenation. At this point 150 gal. of acetic anhydride (about 50% of the total to ultimately be used) was added and the hydrogenation continued at 70° C. until complete. The reaction product was filtered to recover catalyst and passed to the acetylator.

Acetylator

The filtered reaction mixture was passed to a glass lined autoclave at 60° C. and 40 lbs. sodium hydrosulfite added (to destroy nitrites that may have formed). Then the remaining 150 gal. of acetic anhydride was added to complete acetylation at 100° C. The reaction product was cooled to about 25° C. and centrifuged to remove salts or insolubles.

APAP 3500 lbs. of crude wet APAP was recovered representing 83–85% yield. The product had excellent purity and color.

EXAMPLE V

Analysis of APAP Compared to USP Standards

The following analysis compares a typical APAP product produced by the stepwise/boric acid process of this invention with high purity standards. For this example 30 lbs. of p-nitrophenol was hydrogenated at 63°–67° C. by stepwise acetylation using 10 mole percent boric acid and adding 50% acetic anhydride after completing 60% of the hydrogenation. Product yield was about 85%.

| ANALYTICAL RESULTS (Batch B112) | | USP STANDARDS |
|---|---|---|
| Solubility | Passes | To pass |
| Identification | Passes | To pass |
| Melting Range | 168.7–169.7° C. | 168–172° C. |
| Infrared Absorption | Passes | To pass |
| Ultraviolet Absorption | Passes | To pass |
| pH | 5.4 | 5.3–6.5 |
| Water by KF | 0.27% | 0.5% Max. |
| Residue on Ignition | Nil | 0.1% Max. |
| Chloride | Passes | 140 ppm Max. |
| Sulfate | Passes | 200 ppm Max. |
| Sulfide | Passes | No trace |
| Heavy Metals | Passes | 10 ppm Max. |
| RCS | Passes | Matching Fluid A |
| Free PAP | Passes | 0.005% Max. |
| p-Chloroacetanilide | Passes | 10 ppm Max. |
| Assay | 99.91% | 98.0–100.5% |
| | | ADDITIONAL STANDARDS |
| Soln 1/10 EtOH | Passes | Clear, & Colorless |
| 10% EtOH Color | 0–5 APHA | 10 APHA Max. |
| Sat. Water Soln Color | Colorless | Report |
| Caustic Soln. Color | Passes | Report |
| Foreign Substance | 20 ppm | Report |
| Limit of Color | 0.024A | |
| Complete Sulfate (X5) | less than 10 ppm | 200 ppm Max. |
| Insoluble Iron | 0.045 ppm | 0.5 ppm Max. |
| Granulation | Satisfactory | Report |
| Mag. Attr. Part. | 1/100 gms. | Report |

EXAMPLE VI

The following runs further demonstrate the stepwise process of the invention following the procedure as previously described at 65°–72° C. and 60–72 psig with variation summarized in the Table:

| | | Hydrogenation | | | Acetyl'n | | Purity | |
|---|---|---|---|---|---|---|---|---|
| PNP Lbs. | 5% Pd. on Carbon | Temp. °C. | Pressure PSIG | Boric Acid | a % of H$_2$ Absorbed | Recrystal. Yields | Caustic Test | Granulation |
| 35 | 90 gr. | 47–52 | 68–72 | — | 58.0% | 78.6% | Pass | Sl. Pink |
| 38 | 60 gr. | 68–71 | 67–68 | — | 52.6% | 80.0% | Pass | Pass |
| 38 | 100 gr. | 60–70 | 65–69 | — | 50.6% | 86.6% (crude) | Pass (lab sample) | Pass |
| 28.5 | 70 gr. | 63–85 | 60–70 | — | 79.1% | 71.5% | Pass | Sl. Pink |
| 28.5 | 65 gr. | 68–71 | 64–68 | — | 64.8% | 69.4% | Pass | Pass |
| 30 | 44.5 gr. | 63–74 | 68–70 | 1.33# | 60.0% | * | Pass | Pass |

*No yield taken due to filter press plugging toward end of filtration

While the invention has been described in connection with specific embodiments thereof, it will be understood that it is capable of further modifications and this application is intended to cover any variations, uses or adaptations of the invention and including such departures from the present disclosure as come within known or customary practice in the art to which this invention pertains and as may be applied to the essential features hereinbefore set forth, and as fall within the scope of the invention.

I claim:

1. A stepwise process for the production of N-acetyl-p-aminophenol from p-nitrophenol comprising
   (a) reducing p-nitrophenol with hydrogen in a solvent system consisting of water to convert a portion of said p-nitrophenol to p-aminophenol while the pH is below about 7.0;
   (b) acetylating the p-aminophenol from step (a) to N-acetyl-p-aminophenol by adding acetic anhydride to the reaction mixture of step (a) whereby acetic acid is generated in situ in a sufficient amount to maintain the pH below about 7.0;

(c) reducing the remaining p-nitrophenol to p-aminophenol by hydrogenating the reaction mixture of step (b) while the pH is below about 7.0; and (d) acetylating the p-aminophenol from step (c) to N-acetyl-p-aminophenol by adding acetic anhydride to the reaction mixture of step (c) whereby acetic acid is generated in situ in a sufficient amount to maintain the pH below about 7.0.

2. The process according to claim 1 wherein the portion of p-nitrophenol converted to p-aminophenol in step (a) is above about 20% by weight.

3. The process according to claim 1 wherein the portion of p-nitrophenol converted to p-aminophenol in step (a) is from about 50% to about 60% by weight.

4. The process according to claim 1 which further comprises additional reduction and acetylation steps between step (b) and step (c) until the available p-nitrophenol has been exhausted.

5. The process according to claim 1 wherein the pH is from about 2.5 to about 7.0.

6. The process according to claim 1 wherein the temperature for reduction is maintained below about 110° C.

7. The process according to claim 1 wherein the temperature for acetylation is maintained at from about 65° C. to about 75° C.

8. The process of claim 1 wherein the yield of N-acetyl-p-aminophenol from step (d) is at least above about 80% by weight.

9. The process of claim 1 wherein hydrogenation is conducted in the presence of a metal hydrogenation catalyst.

10. The process of claim 9 wherein said catalyst is palladium.

11. The process of claim 10 wherein said catalyst is palladium-on-carbon.

12. The process of claim 1 wherein the p-nitrophenol employed is contained in the hydrolysate product from p-chloronitrobenzene.

13. A stepwise process for the production of N-acetyl-p-aminophenol from p-chloronitrobenzene comprising (a) subjecting p-chloronitrobenzene to alkaline hydrolysis to produce p-nitrophenol;

(b) reducing the p-nitrophenol from step (a) with hydrogen in a solvent system consisting of water and a sufficient amount of borate ion to complex undesirable reaction by-products and using a metal hydrogenation catalyst to convert a portion of said p-nitrophenol to p-aminophenol while the pH is below about 7.0;

(c) acetylating the p-aminophenol from step (b) to N-acetyl-p-aminophenol by adding acetic anhydride to the reaction mixture of step (b) whereby acetic acid is generated in situ in a sufficient amount to maintain the pH below about 7.0;

(d) reducing the remaining p-nitrophenol to p-aminophenol by hydrogenating the reaction mixture of step (c) while the pH is below about 7.0; and (e) acetylating the p-aminophenol from step (d) to N-acetyl-p-aminophenol by adding acetic anhydride to reaction mixture of step (d) whereby acetic acid is generated in situ in a sufficient amount to maintain the pH below about 7.0.

14. The process of claim 13 wherein the amount of borate ion present is from about 0.5 to about 20 mole percent based on the p-nitrophenol.

15. The process of claim 14 wherein the amount of borate ion is from about 10 to about 15 mole percent based on p-nitrophenol.

16. The process of claim 13 wherein the first portion of p-nitrophenol converted to p-aminophenol in step (b) is above about 20% by weight.

17. The process of claim 16 wherein the portion of p-nitrophenol converted to p-aminophenol is from about 50% to about 60% by weight.

18. The process of claim 13 wherein the pH is from about 2.5 to about 7.0.

19. The process of claim 13 wherein the temperature is maintained from about 65° C. to about 75° C.

20. The process of claim 13 wherein the metal catalyst is palladium.

21. The process of claim 13 wherein the yield of N-acetyl-p-aminophenol is at least above about 80% by weight.

22. An improved process for the production of N-acetyl-p-aminophenol which comprises subjecting p-chloronitrophenol to alkaline hydrolysis to produce p-nitrophenol, adding a sufficient amount of borate ion to interact with undesirable by-products of said alkaline hydrolysis, reducing the borate ion containing p-nitrophenol hydrolysis product in the presence of a palladium catalyst to partially convert a portion of said p-nitrophenol to p-aminophenol, acetylating the p-aminophenol to N-acetyl-p-aminophenol, and recovering N-acetyl-p-aminophenol, characterized in that said reducing and acetylating proceeds in a stepwise manner at a pH below about 7.0 and a temperature from about 65° C. to about 75° C. until the conversion of available p-nitrophenol to N-acetyl-p-aminophenol is completed.

* * * * *